United States Patent
Keil

(10) Patent No.: US 11,717,695 B2
(45) Date of Patent: Aug. 8, 2023

(54) HIGH VOLTAGE THERAPY SYSTEM WITH CURRENT CONTROL

(71) Applicant: CARDIAC PACEMAKERS, INC., St. Paul, MN (US)

(72) Inventor: Brandon Tyler Keil, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 260 days.

(21) Appl. No.: 17/173,666

(22) Filed: Feb. 11, 2021

(65) Prior Publication Data
US 2021/0252299 A1 Aug. 19, 2021

Related U.S. Application Data

(60) Provisional application No. 62/976,132, filed on Feb. 13, 2020.

(51) Int. Cl.
*A61N 1/39* (2006.01)
(52) U.S. Cl.
CPC ....... *A61N 1/39622* (2017.08); *A61N 1/3968* (2013.01); *A61N 1/3975* (2013.01)
(58) Field of Classification Search
CPC . A61N 1/39622; A61N 1/3968; A61N 1/3975
See application file for complete search history.

(56) References Cited

U.S. PATENT DOCUMENTS

| | | | |
|---|---|---|---|
| 5,507,781 A | 4/1996 | Kroll et al. | |
| 5,643,323 A | 7/1997 | Kroll et al. | |
| 6,331,794 B1 * | 12/2001 | Blanchard | H03K 17/6871 |
| | | | 327/112 |
| 6,647,292 B1 | 11/2003 | Bardy et al. | |
| 6,721,597 B1 | 4/2004 | Bardy et al. | |
| 6,754,528 B2 | 6/2004 | Bardy et al. | |
| 6,778,860 B2 | 8/2004 | Ostroff et al. | |
| 6,865,417 B2 | 3/2005 | Rissmann et al. | |
| 6,952,608 B2 | 10/2005 | Ostroff | |
| 6,954,670 B2 | 10/2005 | Ostroff | |
| 6,968,231 B1 | 11/2005 | Silvian et al. | |
| 7,149,575 B2 | 12/2006 | Ostroff et al. | |
| 7,330,757 B2 | 2/2008 | Ostroff et al. | |
| 7,555,338 B2 | 6/2009 | Ostroff | |
| 7,783,340 B2 | 8/2010 | Sanghera et al. | |
| 7,860,565 B2 | 12/2010 | Brink | |
| 7,877,139 B2 | 1/2011 | Ostroff | |
| 8,157,813 B2 | 4/2012 | Ko et al. | |
| 8,160,686 B2 | 4/2012 | Allavatam et al. | |
| 8,200,341 B2 | 6/2012 | Sanghera et al. | |
| 8,209,005 B1 * | 6/2012 | Moulder | A61N 1/3925 |
| | | | 607/17 |

(Continued)

*Primary Examiner* — Eric D. Bertram
(74) *Attorney, Agent, or Firm* — Seager, Tufte & Wickhem LLP

(57) ABSTRACT

Improved devices, circuits and methods of operation in implantable stimulus systems. An implantable defibrillator may comprise an H-bridge output circuit having low and high sides, with a current controlling circuit coupled to the high side of the H-bridge output circuit and a current monitoring circuit coupled to the low side of the H-bridge output circuit. A bootstrap design or a DC isolating circuit or circuit element may be used in the current controlling circuit.

13 Claims, 10 Drawing Sheets

(56) References Cited

U.S. PATENT DOCUMENTS

| | | |
|---|---|---|
| 8,463,392 B2 | 6/2013 | Aghassian |
| 8,473,066 B2 | 6/2013 | Aghassian et al. |
| 8,532,785 B1 | 9/2013 | Crutchfield et al. |
| 8,548,590 B2 | 10/2013 | Aghassian |
| 8,565,878 B2 | 10/2013 | Allavatam et al. |
| 8,825,157 B2 | 9/2014 | Warren et al. |
| 8,972,005 B2 | 3/2015 | Rasmussen et al. |
| 8,983,599 B2 | 3/2015 | Garrett et al. |
| 9,283,398 B2 * | 3/2016 | Ostroff ............... A61N 1/39622 |
| 9,579,517 B2 | 2/2017 | Meador et al. |
| 9,641,012 B2 | 5/2017 | Cabelka et al. |
| 9,643,025 B2 | 5/2017 | Crutchfield et al. |
| 9,750,950 B2 | 9/2017 | Norton et al. |
| 9,814,889 B2 | 11/2017 | Strommer et al. |
| 9,861,827 B2 | 1/2018 | Cabelka et al. |
| 9,861,828 B2 | 1/2018 | Norton et al. |
| 9,956,442 B2 | 5/2018 | Cooper et al. |
| 10,046,168 B2 | 8/2018 | Nikolski et al. |
| 10,050,700 B2 | 8/2018 | Ludwig et al. |
| 10,080,905 B2 | 9/2018 | Anderson et al. |
| 10,155,119 B2 | 12/2018 | Anderson et al. |
| 10,159,847 B2 | 12/2018 | Rasmussen et al. |
| 10,213,610 B2 | 2/2019 | Maile et al. |
| 10,350,425 B2 | 7/2019 | Nikolski et al. |
| 10,471,267 B2 | 11/2019 | Thompson-Nauman et al. |
| 10,556,118 B2 | 2/2020 | Anderson et al. |
| 2005/0288714 A1 * | 12/2005 | Ostroff ............... A61N 1/3912 607/9 |
| 2006/0167503 A1 | 7/2006 | Warren et al. |
| 2006/0241698 A1 * | 10/2006 | Ostroff ............... A61N 1/3937 607/2 |
| 2008/0077189 A1 * | 3/2008 | Ostroff ............... A61N 1/3956 607/27 |
| 2010/0280577 A1 * | 11/2010 | Roy ..................... A61N 1/378 323/280 |
| 2010/0324619 A1 * | 12/2010 | Wanasek ............ A61N 1/3625 607/9 |
| 2012/0029335 A1 | 2/2012 | Sudam et al. |
| 2012/0197325 A1 * | 8/2012 | Sauer .................. A61N 1/3981 607/5 |
| 2014/0343625 A1 * | 11/2014 | Laighin ............... A61N 1/36034 607/48 |
| 2016/0166841 A1 * | 6/2016 | Ostroff ............... A61N 1/3912 607/4 |
| 2017/0021159 A1 | 1/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1 | 2/2018 | Reddy |
| 2018/0133462 A1 | 5/2018 | Reddy |
| 2021/0252296 A1 | 8/2021 | Keil et al. |
| 2021/0257849 A1 | 8/2021 | Keil et al. |
| 2021/0283409 A1 | 9/2021 | Keil et al. |

* cited by examiner

HIGH VOLTAGE THERAPY SYSTEM WITH CURRENT CONTROL

CROSS REFERENCE TO RELATED APPLICATIONS

This application claims the benefit of and priority to U.S. Provisional Patent Application Ser. No. 62/976,132 filed on Feb. 13, 2020, the disclosure of which is incorporated herein by reference.

BACKGROUND

Battery powered implantable devices, such as implantable defibrillators, may generate output stimuli having a larger voltage than the batteries of such devices can directly provide. Voltage boosting circuitry is typically used to create the higher voltages, including, for example, switched capacitor and/or transformer-based DC:DC conversion circuitry. In an implantable defibrillator, for example, a DC:DC circuit, such as a flyback transformer circuit, can be used to transfer power from a battery to a high power capacitor stack until the energy stored on the capacitor stack meets a therapy threshold. The stored energy is then discharged to the patient.

When discharging the energy, it is common to deliver therapy in a biphasic pattern that requires switching the direction of current flow. An H-Bridge circuit is often used to provide the switching capability. The switches of an H-Bridge, which may take the form of junction or field effect transistors, silicon controlled rectifiers, or other suitable circuitry, may be used in an ON/OFF manner, in which currents are not controlled, for delivering high power therapy such as defibrillation. It may be desirable in some instances to reuse this circuitry to provide controlled current outputs. New and alternative circuit designs and methods for providing controlled current outputs are desired.

Overview

The present inventors have recognized, among other things, that a problem to be solved is the need for new and/or alternative circuit designs for using and reusing defibrillation output circuitry to deliver controlled current pacing or induction pulses.

A first illustrative and non-limiting example takes the form of an implantable defibrillator comprising a housing and operational circuitry therein, the operational circuitry comprising: at least one battery; at least one high power capacitor; a DC:DC conversion circuit configured to charge the at least one high power capacitor using current drawn from the at least one battery; an H-bridge output circuit comprising first and second high side legs and first and second low side legs, each leg comprising a switch, the first high side and first low side legs coupled together at a first output node, and the second high side and second low side legs coupled together at a second output node; a current monitoring subcircuit coupled to the first and second low side legs, the current monitoring subcircuit adapted to receive current through both of the first and second low side legs; and a current control subcircuit coupling the high power capacitor to the first and second high side legs, the current control subcircuit configured to receive a feedback signal from the current monitoring subcircuit to control current through the H-bridge.

Additionally or alternatively, the current control subcircuit comprises a bootstrap circuit coupled to a first transistor that is configured to enable current flow to the H-bridge from the at least on high power capacitor.

Additionally or alternatively, the first transistor includes a gate, drain and source, the drain coupled to the high voltage power supply, the source coupled to the high side legs of the H-bridge; and the bootstrap circuit comprises: a first diode coupling the source of the first transistor to the gate of the first transistor; a capacitor coupled between the source of the first transistor and a second diode that in turn couples to a voltage source; a first resistor coupling a node between the second diode and the capacitor to the gate of the first transistor; a second transistor configured to receive a control signal related to a feedback signal captured by the current monitoring subcircuit; and a second resistor coupled via the second transistor to ground, the second resistor also coupled to the gate of the first transistor.

Additionally or alternatively, the bootstrap circuit comprises: a first transistor with a gate, drain and source, the drain coupled to the high voltage power supply, the source coupled to the high side legs of the H-bridge; a first diode coupling the source to the gate; a capacitor coupled between the source and a second diode that in turn couples to a voltage source; a first resistor coupling the node between the second diode and the capacitor to the gate; and a second transistor coupled to the gate of the first transistor, the second transistor configured to receive a control signal related to a feedback signal captured by the current monitoring subcircuit.

Additionally or alternatively, the current sensing circuit comprises a sense resistor coupled to the low side of the H-bridge to thereby create a voltage when current flows through the sense resistor, providing feedback to the current control circuit, further comprising a bypass path parallel to the sense resistor, the bypass path comprising one or more diodes allowing current to flow above a diode voltage, wherein the implantable defibrillator comprises a control module operable as follows: during defibrillation shock delivery, the feedback signal from the current sensing circuit is not used to control operation of the first transistor; and during pacing delivery, the feedback signal from the current sensing circuit is used to control operation of the first transistor.

Additionally or alternatively, the current control subcircuit comprises a high voltage isolation component having an input electrically coupled to the feedback signal from the current monitoring subcircuit, and an output floating relative to the input, wherein the output is delivered to a first transistor that controls current flow from the at least one high power capacitor to the H-bridge. In select examples, the high voltage isolation component may be a transformer or an optical isolator.

Additionally or alternatively, the device may further comprise an enable switch, wherein the current control subcircuit comprises a first transistor for controlling current, wherein the enable switch couples the at least one high voltage capacitor to the first transistor, which in turn couples to the high side of the H-Bridge.

Additionally or alternatively, the device may further comprise an enable switch, wherein the current control subcircuit comprises a first transistor for controlling current, wherein the first transistor couples the at least one high voltage capacitor to the enable switch, which in turn couples to the high side of the H-Bridge.

Additionally or alternatively, the device may further comprise an enable switch, wherein the current control subcircuit comprises a first transistor for controlling current, wherein the first transistor couples the at least one high voltage capacitor to the enable switch, which in turn couples to the high side of the H-Bridge.

A second illustrative and non-limiting example takes the form of an electronic circuit for providing an output in a medical device comprising: at least one high power capacitor; an H-bridge output circuit comprising first and second high side legs and first and second low side legs, each leg comprising a switch, the first high side and first low side legs coupled together at a first output node, and the second high side and second low side legs coupled together at a second output node; a current monitoring subcircuit coupled to the first and second low side legs, the current monitoring subcircuit adapted to receive current through both of the first and second low side legs; and a current control subcircuit coupling the high power capacitor to the first and second high side legs, the current control subcircuit configured to receive a feedback signal from the current monitoring subcircuit to control current through the H-bridge.

Additionally or alternatively, the current control subcircuit comprises a bootstrap circuit coupled to a first transistor that enables current flow to the H-bridge from the at least on high power capacitor.

Additionally or alternatively, the first transistor includes a gate, drain and source, the drain coupled to the high voltage power supply, the source coupled to the high side legs of the H-bridge; and the bootstrap circuit comprises: a first diode coupling the source of the first transistor to the gate of the first transistor; a capacitor coupled between the source of the first transistor and a second diode that in turn couples to a voltage source; a first resistor coupling a node between the second diode and the capacitor to the gate of the first transistor; a second transistor configured to receive a control signal related to a feedback signal captured by the current monitoring subcircuit; and a second resistor coupled via a second transistor to ground, the second resistor coupled to the gate of the first transistor.

Additionally or alternatively, the first transistor includes a gate, drain and source, the drain coupled to the high voltage power supply, the source coupled to the high side legs of the H-bridge; and the bootstrap circuit comprises: a first diode coupling the source of the first transistor to the gate of the first transistor; a capacitor coupled between the source of the first transistor and a second diode that in turn couples to a voltage source; a first resistor coupling a node between the second diode and the capacitor to the gate of the first transistor; and a second transistor coupled to the gate of the first transistor, the second transistor configured to receive a control signal related to a feedback signal captured by the current monitoring subcircuit.

Additionally or alternatively, the current sensing circuit comprises a sense resistor coupled to the low side of the H-bridge to thereby create a voltage when current flows through the sense resistor, providing feedback to the current control circuit, further comprising a bypass path parallel to the sense resistor, the bypass path comprising one or more diodes allowing current to flow above a diode voltage, wherein the implantable defibrillator comprises a control module operable as follows: during defibrillation shock delivery, the feedback signal from the current sensing circuit is not used to control operation of the first transistor; and during pacing delivery, the feedback signal from the current sensing circuit is used to control operation of the first transistor.

Additionally or alternatively, the current control subcircuit comprises a high voltage isolation component having an input electrically coupled to the feedback signal from the current monitoring subcircuit, and an output floating relative to the input, wherein the output is delivered to a first transistor that controls current flow from the at least one high power capacitor to the H-bridge. In select examples, the high voltage isolation component may be a transformer or an optical isolator.

Additionally or alternatively, the circuit may further comprise an enable switch, wherein the current control subcircuit comprises a first transistor for controlling current, wherein the enable switch couples the at least one high voltage capacitor to the first transistor, which in turn couples to the high side of the H-Bridge.

Additionally or alternatively, the circuit may further comprise an enable switch, wherein the current control subcircuit comprises a first transistor for controlling current, wherein the first transistor couples the at least one high voltage capacitor to the enable switch, which in turn couples to the high side of the H-Bridge.

Additionally or alternatively, the circuit may further comprise an enable switch, wherein the current control subcircuit comprises a first transistor for controlling current, wherein the first transistor couples the at least one high voltage capacitor to the enable switch, which in turn couples to the high side of the H-Bridge.

A third illustrative and non-limiting example takes the form of an implantable medical device comprising a conductive housing having a port for receiving a lead, the conductive housing containing a power source and the electronic circuit of the second illustrative and non-limiting example (and/or any of the above additions or alternatives thereto), wherein the H-bridge is coupled to the conductive housing to provide a first output therethrough and to the port to provide a second output therethrough. The implantable medical device may be an implantable pacemaker defibrillator.

A fourth illustrative and non-limiting example takes the form of a method of operation in an implantable medical device for delivering an output from the device, the device including a power source, a charging circuit, and a capacitor, the charging circuit coupled to the power source to receive power therefrom and to the capacitor to store therapeutic energy thereon, the device further including: an H-bridge output circuit comprising first and second high side legs and first and second low side legs, each leg comprising a switch, the first high side and first low side legs coupled together at a first output node, and the second high side and second low side legs coupled together at a second output node; a current monitoring subcircuit coupled to the first and second low side legs, the current monitoring subcircuit adapted to receive current through both of the first and second low side legs; and a current control subcircuit coupling the high power capacitor to the first and second high side legs, the current control subcircuit configured to receive a feedback signal from the current monitoring subcircuit to control current through the H-bridge; the method comprising operating in a current controlled output mode by: charging the capacitor to a predetermined energy level; enabling a selected set of high and low side switches of the H-Bridge; after enabling the selected set of high and low side switches of the H-Bridge, enabling the current control subcircuit to generate an output; receiving a current in the current monitoring subcircuit and providing a feedback signal; and using the feedback signal to modulate current through the current control subcircuit.

Additionally or alternatively, the current control subcircuit comprises a bootstrap circuit coupled to a first transistor that enables current flow to the H-bridge from the at least on high power capacitor, wherein the step of enabling the current control subcircuit comprises using the bootstrap circuit to keep the first transistor in a state of allowing current flow as voltage at a node coupling the first transistor to the H-bridge rises due to current flow.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
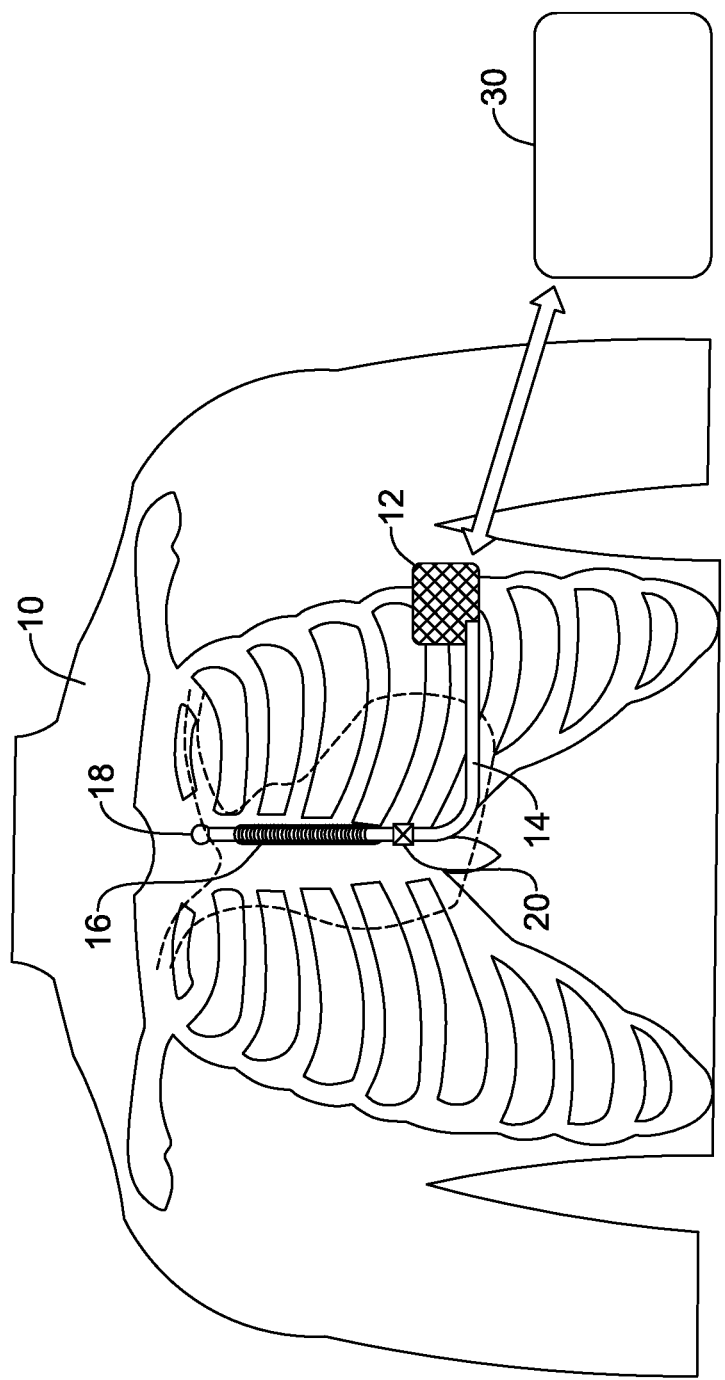
FIG. 1 shows an implantable stimulus system relative to the torso of a patient.

FIG. 1 shows an implantable stimulus system relative to the torso of a patient 10. In the example shown, an implantable canister 12 is placed near the left axilla, with a lead 14 extending medially therefrom. The lead 14 turns near the xiphoid to advance in a superior direction, toward the head generally parallel the sternum and over the heart. The lead 14 is shown illustratively as having a defibrillation coil electrode 16 and distal and proximal sense electrodes 18, 20. An external programmer 30 can wirelessly communicate with the canister 12 to provide therapy and sensing instructions to the system and to check various device status, history and diagnostic factors. The present invention is not limited to the specific lead 14 design shown, nor position of either the lead 14 or canister 12, and a variety of details and alternatives are disclosed in the patents and applications cited in the following paragraph, each of which may be used in various embodiments of the present invention.

The example of FIG. 1 shows the lead 14 placed over the ribs, in a subcutaneous position. Other subcutaneous positions may be used, such as described in US PG Pat. Pub. No. 20120029335, and U.S. Pat. Nos. 8,157,813, 7,149,575, 6,721,597, and 6,647,292, the disclosures of which are incorporated herein by reference. In other examples, the lead may be placed beneath the sternum in a substernal position, in the mediastinal space, as described in US PG Pat. Pub. No. 20170021159, and/or U.S. Pat. No. 10,471,267, the disclosure of which are incorporated herein by reference. In still other examples, the internal thoracic vasculature (including the internal thoracic vein or ITV) may be used for implantation as a final placement or as an avenue to the mediastinum, as described in US PG Pub. Nos. 20180133462, 20180036547, 20180036527, the disclosures of which are incorporated herein by reference. Such systems use sensing and therapy electrodes disposed in positions that neither contact nor enter the heart.

Approaches that use pacing electrodes that neither enter nor contact the cardiac tissue call for increased pacing amplitude when compared to transvenous, intracardiac or epicardial electrodes. Historically two separate output paths would be used for an implantable transvenous defibrillator having both pacing and defibrillation therapy capabilities, with a low voltage pacing therapy deliverable directly off of the battery stack or with a limited voltage boost, while a transformer-based circuit would be used to transfer power from the battery to a high voltage (HV) capacitor or capacitor stack for defibrillation purposes. However, with increased pacing amplitude needed for these newer, substernal, ITV, extracardiac or subcutaneous pacing configurations, the prior solutions become less usable.

For example, with the SICD System™, three series batteries are used in the device, providing a nominal output voltage in the range of 9 to 9.5 volts, under light load; the pacing output of this system, used in the post-defibrillation shock context, delivers a 200 mA pacing output into a range of impedances from 25 to 200 ohms (assuming impedance measured during shock delivery), which means pacing can be delivered at up to 40 volts, more than four times the battery voltage. As commercially available, pacing in the SICD System™ is used in a post-shock context for a limited period of time. However, pacing in that system, and others, may be used for any of bradycardia support (chronic or post-defibrillation), as an anti-tachyarrhythmia pacing therapy, or for alleviation of heart failure systems, such as resynchronization therapy, without limitation.

Pacing is delivered at a relatively low duty cycle; a higher duty cycle, such as when inducing fibrillation for testing purposes (as is common at implant), can use a higher duty cycle, requiring still more DC:DC boosting capability. Induction testing is performed to show that an implanted system can both detect an inducted arrhythmia and convert ventricular fibrillation to a normal rhythm with therapeutic shock. In the realm of transvenous defibrillators, there is a trend away from universal induction testing. However, induction testing continues to be commonly used, and in particular can be expected to be a continued practice with newer substernal, ITV, extracardiac and/or subcutaneous defibrillation systems.

Some proposals include adding a separate "pacing therapy" boost circuit and capacitor array to provide intermediate level power for pacing purposes. However, provision of multiple, separate circuits to provide the needed boosting increases complexity, cost, and space requirements, as well as complicating other factors such as reliability. A transformer-based circuit can be used to transfer very large amounts of power from a battery to a capacitor stack, and this technology is widely used in implantable defibrillators today to provide higher power cardioversion and/or defibrillation therapy outputs. Moreover, the commonly used output circuit for defibrillation therapy, which is called an H-bridge due to its shape, having first and second high side legs that meet at first and second load nodes with first and second low side legs, is already present in the device. New and better ways to facilitate multiple output levels, without overly complicating the apparatus, are desired.

While the development of the present invention may focus generally on some of the newer implant positions (subcutaneous, substernal, mediastinal or ITV), the present invention may also be used in more therapy systems with still older implantation positions, including epicardial or transvenous systems having leads and/or electrodes located in or on the heart. In addition, the present invention may also be used in wearable or external medical device systems, such as, but not limited to, wearable, automated external, and clinical/hospital defibrillators.

Figure 2:
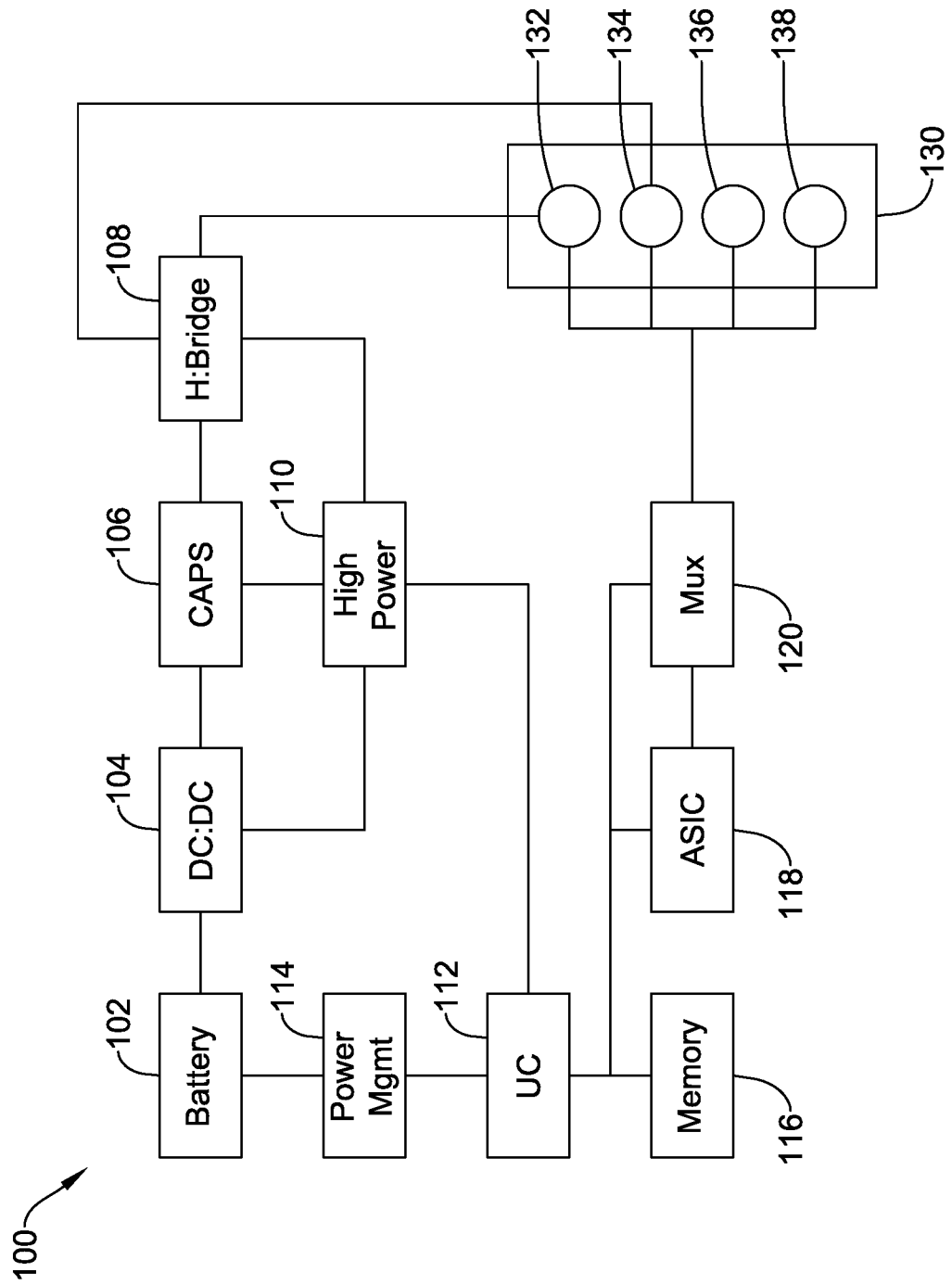
FIG. 2 shows an illustrative block diagram for an implantable stimulus system.

FIG. 2 shows an illustrative block diagram for an implantable stimulus system. The illustrative system 100 is powered by an internal battery 102, which may be of any suitable chemistry for an implantable medical device, such as any of various lithium chemistries (Lithium-Ion, LiMnO2, etc.). The battery 102 may comprise any suitable number of battery cells, such as 1, 2, 3, 4 or more cells. The battery 102 in the example is a non-rechargeable battery; in other examples a rechargeable battery may be used and, if so, a recharging circuit comprising, for example, an inductive coil that can be energized by an external coil may be used, such as described in U.S. Pat. No. 9,814,889 and/or as such systems are known for spinal cord stimulation such as in U.S. Pat. Nos. 8,548,590, 8,473,066 and/or 8,463,392, the disclosure of which are incorporated herein by reference.

The battery 102 can be used for high power therapy delivery by routing the battery output to a DC:DC converter 104 to charge a capacitor stack 106, with an H-Bridge used to issue therapy pulses via electrodes coupled to ports 132, 134. Optionally, in some examples, blocks 104, 106 and 108 reside on a high power hybrid (circuit board) 110 separate from lower power circuitry to reduce interference, among other benefits.

In some examples, a transformer is used as the DC:DC charging circuit, using a flyback transformer layout in which the battery output is directed to a primary coil of the transformer and one or more secondary coils each charge a capacitor of the capacitor stack 106. In operation, the charging sequence alternates between primary and secondary phases. During the primary phase, the transformer receives power from the battery 102, with current passing from the battery, through at least a switch and the transformer to ground. During the secondary phase, the switch is opened, causing an open circuit of the transformer primary coil, driving the energy stored in the transformer during the primary phase into the capacitor stack 106. Appropriately placed diodes can be used to manage current flow and ensure appropriate charging takes place. Switching between primary and secondary phases can be controlled via a timing schedule, or may occur in response to measured currents reaching upper or lower thresholds, or a combination of both, such as having a fixed interval primary phase and a current controlled secondary phase.

While several references herein are to a capacitor stack 106, having, for example, anywhere from 2-6 capacitors, or more, a single capacitor may be used if desired. The drawing indicates dedicated output or output ports 132, 134 which may be, for example, an output coupled to a conductive canister (or portion thereof) that contains the circuitry 100 and an electrode on a lead. In other examples, two lead electrodes, or two housing electrodes, or more than two electrodes may be used for therapy delivery; additional switching circuitry may be used to direct therapy outputs as desired.

In the illustrative example, lower power circuitry is (optionally) powered by a power management block 114 that provides regulated voltages off of the battery 102, such as, for example and without limitation, 1.8, 3.2, 5.1, or other voltages, which are typically reduced relative to the battery output to ensure stable voltages over the useful life of the device, during which the battery voltage typically degrades. Some examples may also include, for example, a 15 volt supply that can be generated by a switched capacitor voltage booster (assuming the battery 102 provides less than 15 volts). A plurality of such power supplies may be included to address various needs in the system, such as, for example and without limitation, providing a 5-volt supply to power a telemetry antenna while a 3.2 volt supply powers a microcontroller.

A microcontroller 112 may be provided for managing various device operations, with a memory 116 provided to store executable instructions as well as device history data, such as measured battery voltages and recorded cardiac data related to "episodes" in which therapy is delivered, as well as any other information or instructions used in the system. An application specific integrated circuit (ASIC) 118 is illustratively shown and, without intending to limit the invention any particular one of these items, may include circuits dedicated to particular tasks, such as an input ECG circuit that filters, amplifies and digitizes sensed signals. Other circuits on the ASIC may include dedicated beat detection circuitry, and/or dedicated morphology analysis circuitry such as a correlation analysis or wavelet comparison circuit. The ASIC 118 may comprise or be coupled to telemetry circuitry using, for example, Medradio, inductive telemetry, or Bluetooth (including Bluetooth Low Energy) communication circuitry. The power management block 114, or portions thereof, may be integrated into the ASIC 118 if desired. In some implementations, the ASIC is used to perform and/or manage ongoing operations of the system as the microcontroller is generally kept in a low power or sleep mode, and the ASIC can issue periodic or occasional signals to wake up the microcontroller as for example may occur when a new heartbeat occurs, or when a calculated heart rate crosses a high rate threshold, or a signal is received on telemetry circuitry indicating the initiation of a communication session, among other triggers for microcontroller wakeup.

A switching circuit is also shown as a multiplexor 120 for coupling to a plurality of inputs/outputs 130, shown as four input/output lines 132, 134, 136, 138; more or fewer input/output lines may be included. In some examples the switching circuitry is used to select one or more sensing vectors defined by pairs or groups of electrodes used for sensing purposes, such as disclosed, for example, in U.S. Pat. Nos. 8,825,157, 7,783,340, 8,200,341, and/or US PG Pat. Pub. Nos., 20170113053, 20170113050, 20170113040, and/or 20170112399, the disclosures of which are incorporated herein by reference.

Figure 3:
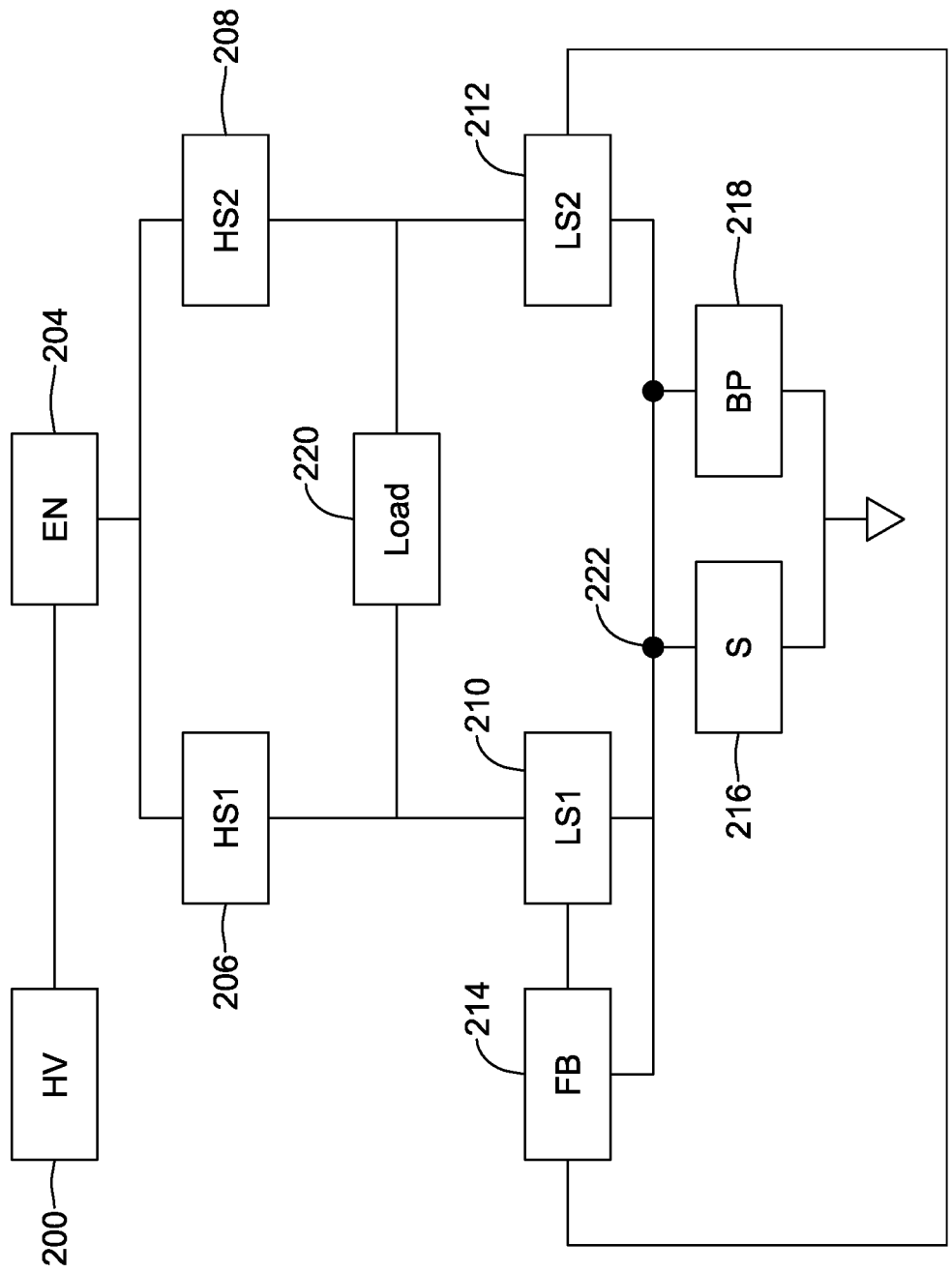
FIG. 3 shows a prior art output circuit.
Figure 4:
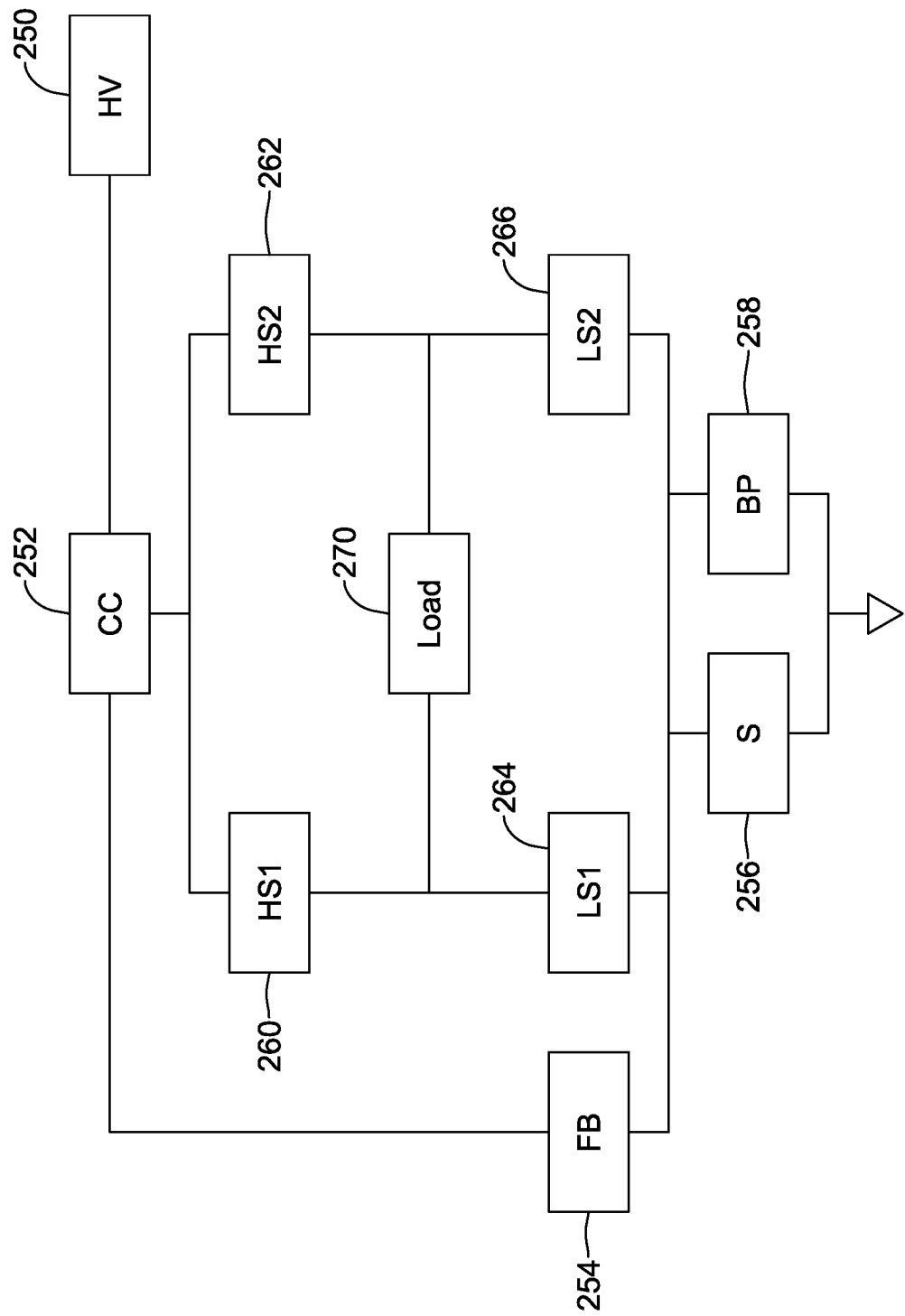
FIGS. 4-7 illustrate new output circuit designs.

FIG. 3 shows a prior art output circuit. The illustrative circuit delivers power from the HV Capacitors 200 to a load 220, which represents the patient. An enable switch 204 sit outside (above) the H-Bridge, which comprises two high side switches 206, 208 and two low side switches 210, 212. In this example, the low side switches 210, 212 can be used as ON/OFF switches during defibrillation, and can be used to control current during pacing and induction processes by the use of a feedback circuit 214. Between the H-Bridge and ground are a sense resistor 216 and a bypass switch 218.

To issue therapy, a combination of the enabling switch 204 and one high side and one low side switch are closed. In a first polarity output, switches 204, 206 and 212 are closed; to deliver output of the opposite polarity, switches 204, 208 and 210 are closed. During defibrillation therapy, the sense resistor 216 is bypassed by closing the bypass switch 218, and current flow is determined by the voltage from the HV Caps divided by the impedance of the load 220 and any line impedance/parasitics, which are generally small relative to the load 220. Biphasic therapy can be issued by monitoring the HV Caps 200 to determine when a threshold voltage for switching polarity is reached, such as 40, 50, 60, or 70% (or other value) drop in voltage. For controlled current pacing and induction purposes, the bypass switch 218 is opened, forcing current through the sense resistor 216. The feedback circuit 214 obtains a sense signal from the sensing node 222 and provides a controlled enabling voltage to one of the low side switches 210, 212 (depending on which polarity of output is active) to keep the voltage at node 222 fixed to a predetermined value. For example, when the voltage at node 222 is lower than a target value, that means less than a target current is flowing through sense resistor 216, so the voltage provided to enable whichever of switches 210, 212 is being operated is increased until the voltage at node 222 reaches the target value. To limit the amount of power that has to be absorbed by switches 210, 212, the HV caps 200 are charged for pacing and induction to a voltage that is lower than that used for defibrillation, as, for example, by charging to a level that will enable current to reach the target value for the maximum allowable load impedance. For example, if the maximum allowable, or expected, load is 200 ohms and the current to be issued is 200 mA, then the HV caps 200 may be charged to a value that exceeds 40 volts plus 200 mA times the impedance value of the sense resistor 216, such as, for example and without limitation, 100-200 volts, which would allow for some parasitic losses and avoids current droop as the voltage on the HV caps 200 may drop during therapy output due to current being drawn.

A drain circuit for the HV caps 200 is omitted in the drawing, but may be understood as comprising one or two resistive branches. In a two-branch version, a passive drain branch having a large impedance (1 Mohm, for example) provides a slow drain on the HV capacitors to ensure that a large voltage is not held indefinitely, while a smaller resistor (10 kohm, for example) is provided in series with a switch to allow the HV caps 200 to be drained to a reduced voltage if needed, for example, to allow pacing therapy output after a defibrillation shock if reduced HV cap voltage is desired during pacing relative to the residual voltage after defibrillation shock. Another context for using an active drain branch may be if a patient undergoing induction testing spontaneously converts to normal rhythm while the HV caps 200 are being charged, in which case is may be desirable to drain the HV caps 200 prior to the next induction attempt.

In this circuit, because the low side switches 210, 212 are used to control current flow, they have to absorb a significant amount of power in the controlled current mode, and typically relatively large IGBT devices are used. Also in this circuit, the high side switches 206, 208, and the enable switch 204, are subject to a level shift during therapy output, as the load raises the emitter voltage on each to, practically speaking, the voltage on the HV Caps 200. Therefore an isolation circuit element, such as a transformer or optical isolator, is typically used to provide the control signal to each switch 204, 206, 208, reliant on a low voltage input. The use of larger IGBT elements and the isolation elements increases cost and size of the circuit, and the isolation circuits may also add to the potential for quality issues, as optical isolators can be subject to thermal issues during manufacturing. Alternatives are desired.

It should be understood that an H-bridge, as that term is used, may have more than two high and/or low side legs to allow the use of more than one output vector, if desired. References herein to first and second high and/or low side legs of an H-bridge should be understood as not limiting to just two such legs.

Figure 8:
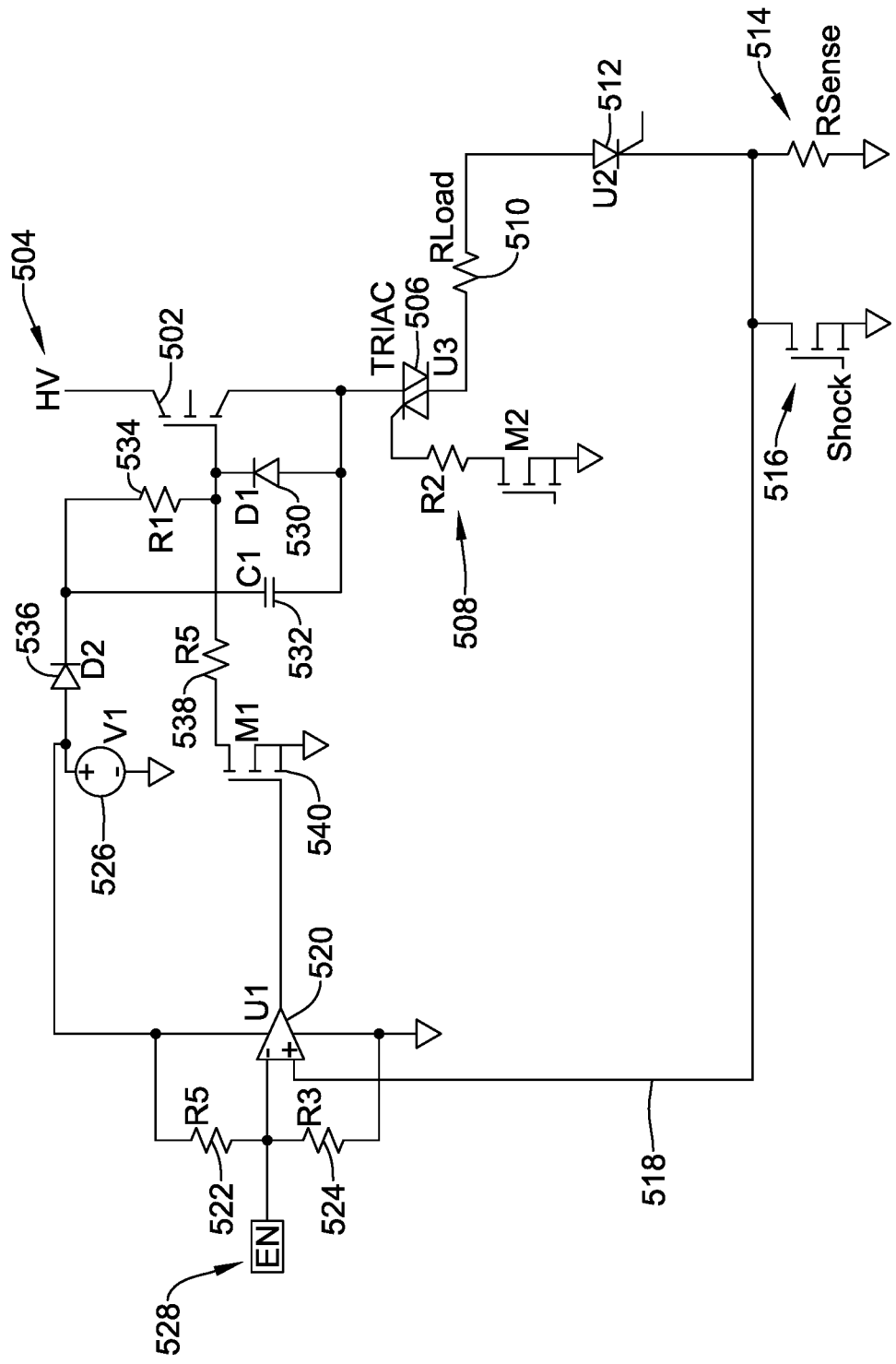
FIGS. 8-10 show subcircuits for current control coupled to the high side of the H-Bridge.
Figure 9:
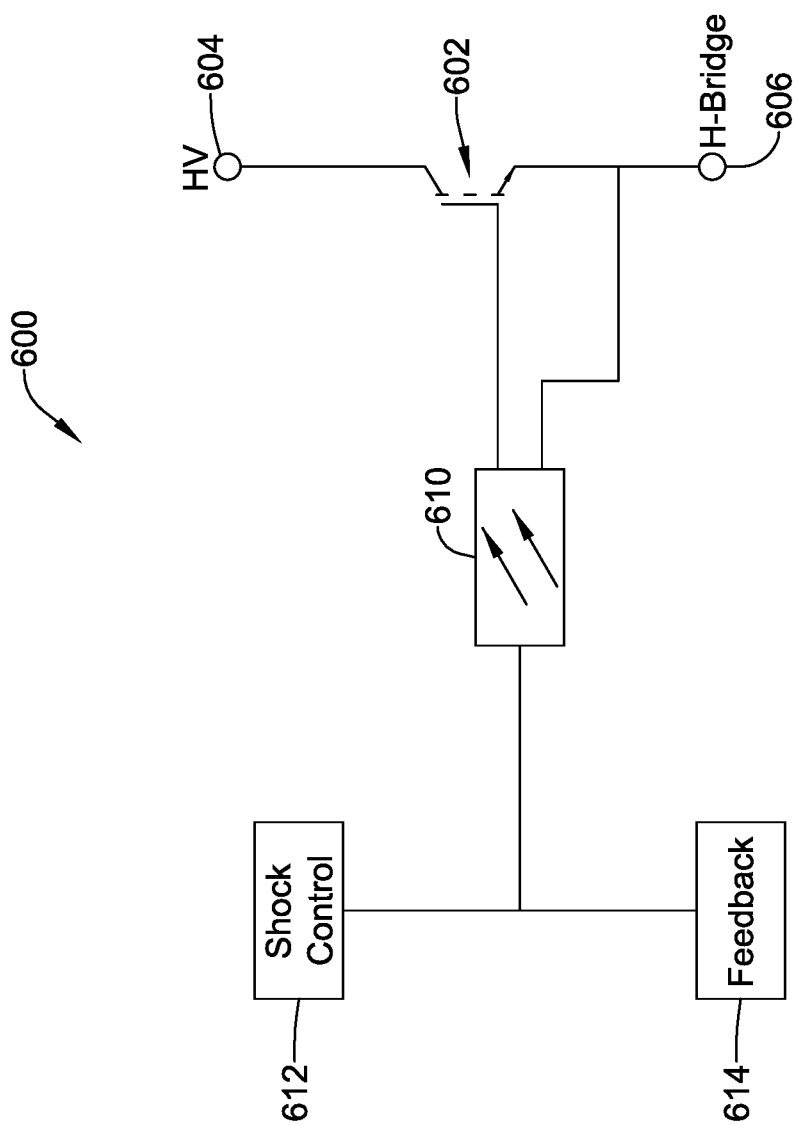
Figure 10:
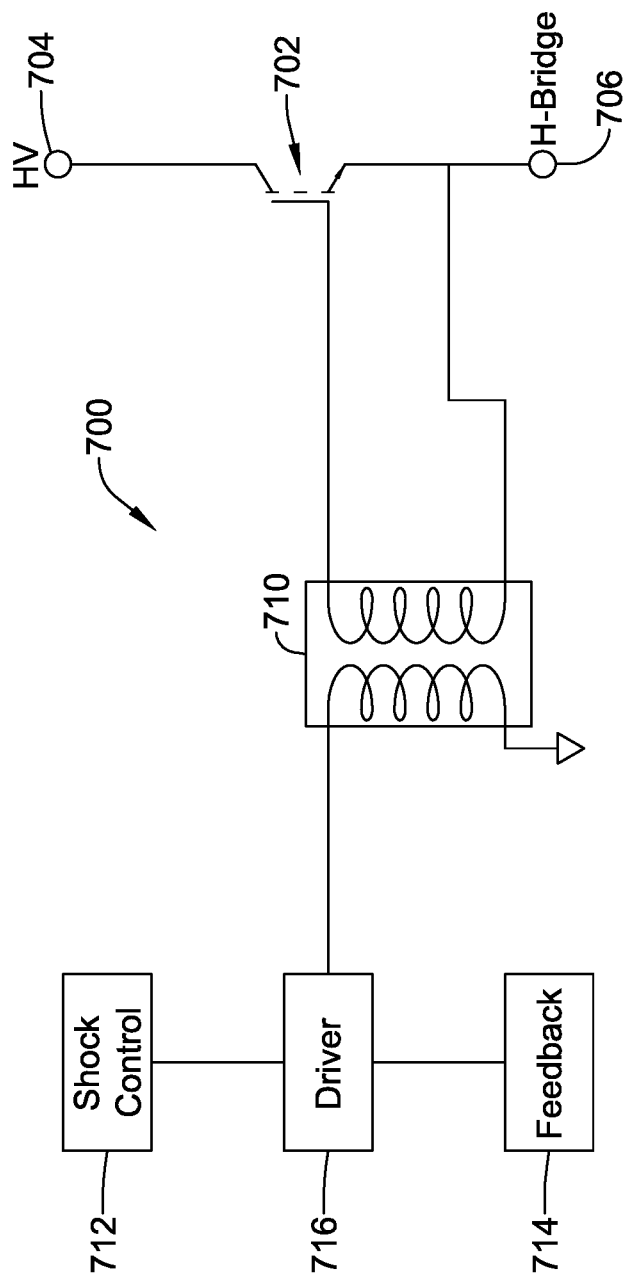

FIGS. 4-7 illustrate new output circuit designs. Starting with FIG. 4, the output circuit design here again delivers power from the HV Caps 250 to a load 270 using an H-Bridge that includes high side switches 260, 262 and low side switches 264, 266. In place of the enable switch shown in FIG. 3, a current control switch 252 is shown sitting above the H-bridge, taking an input from a feedback circuit 254. The H-Bridge is coupled, as before, to a sense resistor 256 in parallel to a bypass switch 258 which in turn couple to ground. The H-bridge itself operates more or less as in FIG. 3 for defibrillation, with the current control switch 252 provided with an enabling signal that places it in an ON state, and either a first polarity output is generated by closing switches 260, 266, or a second polarity output is generated by closing switches 262, 264, while the bypass switch 258 is closed to run current directly to ground. For pacing purposes, the bypass switch 258 is opened, routing current through the sense resistor 256 and providing a sense signal to the feedback circuit 254. The current control switch 252 is then used to manage current flow during therapy delivery. FIGS. 8-10, below, provide details on implementations of the feedback circuitry 254 used to manipulate the current through block 252. In this implementation, the H-Bridge switches can be simplified to use, for example, thyristors or silicon controlled rectifiers (SCR), as desired, which are typically cheaper and smaller than the IGBT devices used in FIG. 3.

In some examples, the sense resistor 256, with or without the bypass switch 258, may be described as a current monitoring subcircuit. A current monitoring subcircuit may further comprise, for example, a comparator or an analog-to-digital convertor. A comparator may be used, for example, to compare the voltage across the sense resistor 256, to a predetermined voltage, or a controllable voltage, and provides an indication of whether the voltage through the sense resistor (which is directly proportional to the current therethrough) is above or below a target or threshold that the predetermined or controllable voltage is indicative of. An analog to digital convertor, if used, provides a measurement output in digital form telling the system controller what voltage has been measured; again, the voltage through the sense resistor would be directly proportional to the current, and knowing the resistance value of the sense resistor, simple division allows the current to be calculated. Thus, for example and without limitation, if a comparator is used, and a 50 ohm resistor is used as sense resistor 256, to obtain a 100 milliamp current, the predetermined or controllable voltage may be 5 volts. In another example, an inductive current measuring apparatus is placed in series with the H-Bridge, using, for example, a Hall effect device or flux gate sensor to sense current flow, with or without a bypass switch.

In some examples, rather than using a bypass switch at 258, one or more diodes or rectifiers may be used instead of a switch. For example, a forward biased diode/rectifier, or reverse biased Zener diode, may be used in place of a switch at 258, as long as the sense resistor in 256 has sufficient current carrying capacity to accommodate however much current would flow during defibrillation due to the forward voltage of the diode/rectifier (or reverse breakdown voltage if a Zener diode is used). Thus, for example, if the feedback circuit 254 is configured to sense a voltage of 3 volts or less, a diode having a forward voltage greater than 3 volts (or two or more diodes in series that sum to a 3 volt forward bias) may be used instead of a bypass switch at 258, simplifying the control setup. Such a substitution may be used in any of the examples herein.

Figure 5:
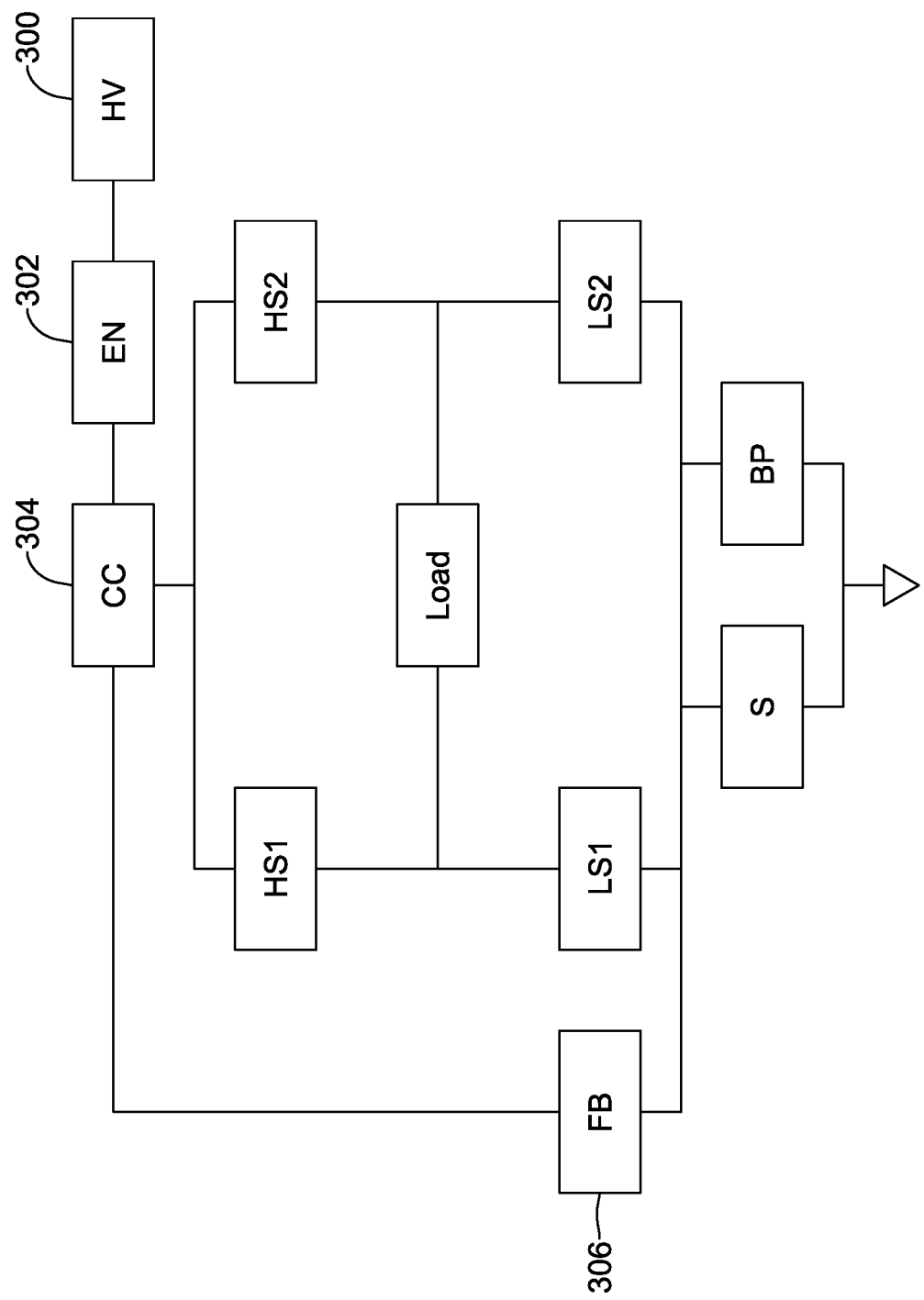

FIG. 5 shows another alternative. Here, an enable switch 302 is also provided between the HV caps 300 and the current control switch 304, again with the current control switch 304 managed by a feedback block 306. The use of a separate enable switch 302 may help to limit leakage current during charging and may shield the components of the current control switch 304 and associated driver/feedback circuit 306 from voltage swings during charging of the HV caps 300.

Figure 6:
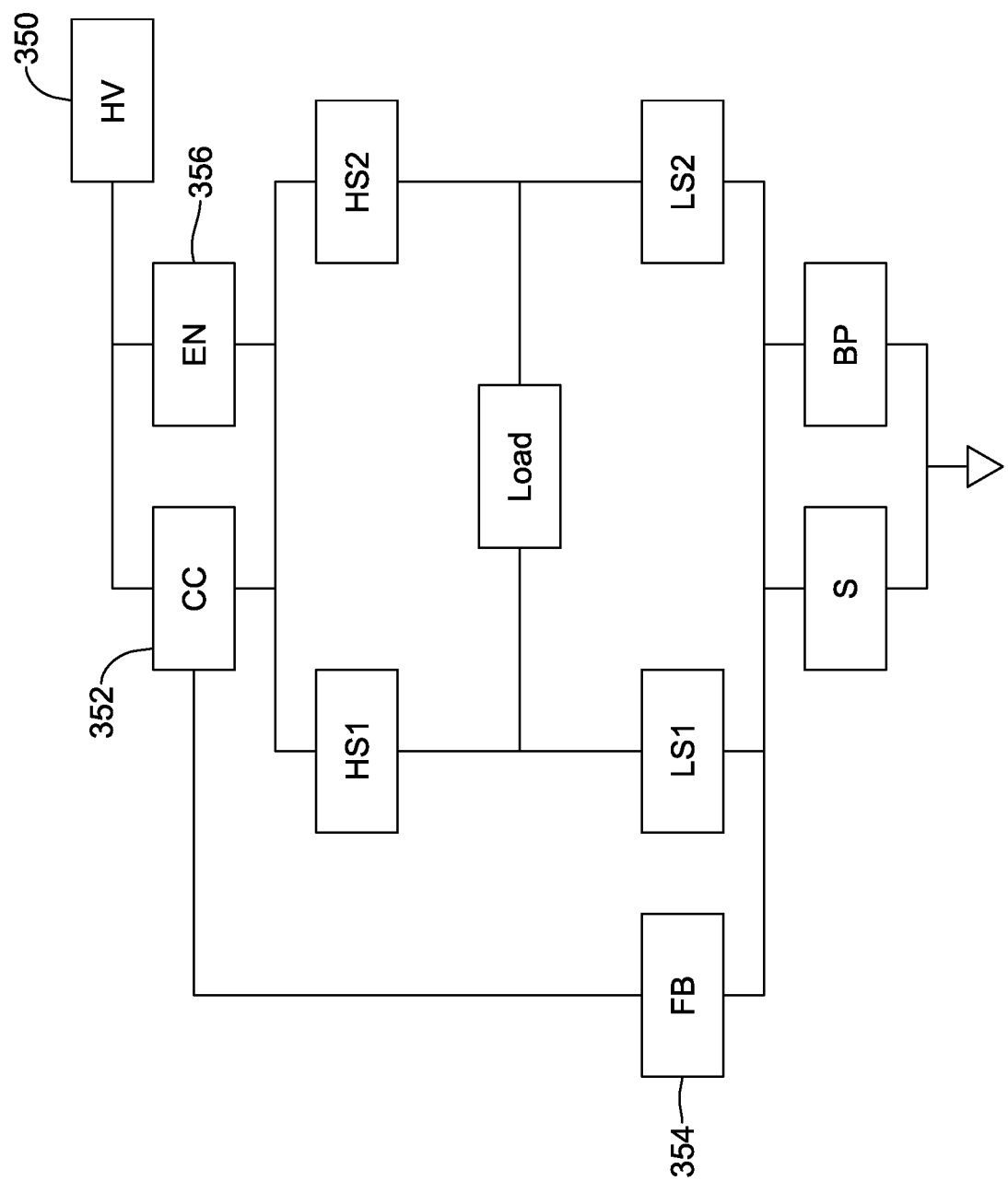

A different configuration is shown in FIG. 6 with the current control switch 352 can be coupled between the HV caps 350 and the H-bridge in parallel with an enable switch 356, again using a feedback circuit 354 to control the current control switch 352. In this example, the current control circuit 352 may be used to preload the H-bridge with small currents of a few milliamps, allowing turn-on of the thyristors or SCRs in the H-bridge before enabling, with switch 356, defibrillation therapy. Such an approach may limit impact of the defibrillation pulse turn-on on system ground. In another example, the maximum current capability of the current control switch 352 may, in the example of FIG. 6, be reduced, as defibrillation currents may approach or exceed 1 ampere. By routing such large peak currents through a separate path, the design may allow a less expensive or smaller current control switch 352 to be used than in other examples.

Figure 7:
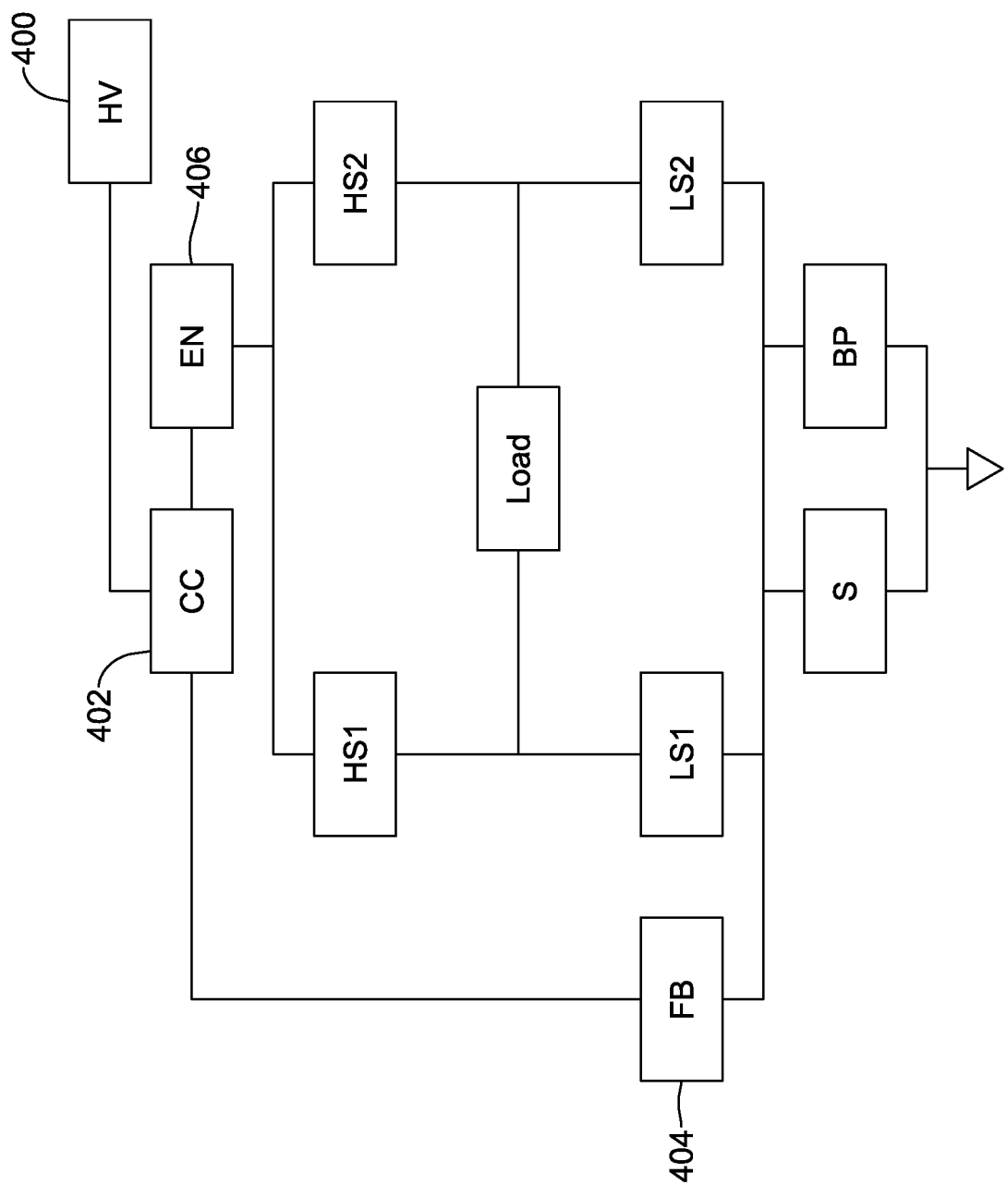

FIG. 7 shows another alternative configuration, in which the current control switch 402 is between the HV caps 400 and the enable switch 406, which in turn couples to the H-Bridge. This example may be useful as a configuration where a bootstrapping circuit used to control the current control switch 402 can be stabilized by the high voltage reaching the current control circuit before the enable switch 406.

FIGS. 8-10 show subcircuits for current control coupled to the high side of the H-Bridge. FIG. 8 generally shows an output circuit including a bootstrap circuit for providing a signal to the gate of the current control switch 502, which receives a signal from the HV caps 504 and routes output current for the device to an H-Bridge, of which one upper leg is shown at 506, with a Triac-type thyristor at 506 receiving an enable signal from a circuit shown at 508. Current in the partially shown H-Bridge goes to the patient load at 510 and then through a low side SCR shown at 512. The other high side leg, and the other low side leg, are omitted to simplify the drawing but the skilled person will recognize how each would be included similar to layouts for H-Bridges shown in FIGS. 3-7. At the low side of the H-Bridge, a bypass or shock switch is shown at 516 parallel to a sense resistor 514.

The feedback circuit is provided with connection 518 provided to an operational amplifier at 520 on the non-inverting input. The inverting input at amplifier 520 is connected to a voltage divider with resistors 522, 524 taking a voltage from a voltage source at 526. For fine tuning the output, the voltage source 526 may be a digital to analog converter, for example, or either of the resistors 522, 524 may be a variable resistor; optionally the voltage source 526 may be configured or calibrated during manufacturing to ensure appropriate control over the current output. The voltage source 526 is also connected via a diode 536 to a capacitor 532 which is in turn connected to the emitter of the current control switch 502. The gate to the current control switch 502 is connected by a diode 530 to its emitter as well. A resistor 534 connects the node at the junction of diode 536 and capacitor 532 to the gate of current control switch 502, and another resistor 538 connects the gate to a transistor at 540, which connects to ground. In an alternative configuration, the resistor at 538 may be omitted and the transistor at 540 couples directly to the gate of transistor 502.

When the HV circuit is charged to a therapy voltage, whether for pacing or defibrillation, the current control switch 502 remains open—that is, not conducting—until enabled. A voltage source 526 is coupled/turned on, but switch 540 is held in a closed state until an enable signal 528 is applied (in the example a low or ground signal is applied), causing switch 540 to open. When switch 540 opens, the capacitor 532 receives and stores the voltage from source 526, less the voltage for diode 536, as does the gate for the current control switch 502, but no current flows through the H-Bridge until the switches in the H-Bridge are enabled. Thus the gate to emitter voltage for the current control switch 502 is raised to a level allowing current to flow.

When the H-Bridge switches are enabled (which may happen first, prior to enabling of switch 540, using enable signals to the H-Bridge switches that are delivered for a duration longer than the expected turn-on-time of the bootstrap circuit and switch 502), the current control switch 502 starts to transmit current from the collector to the emitter and the voltage at the emitter of the current control switch 502 increases. Due the voltage on capacitor 532, the gate voltage on the current control switch 502 is increased to remain above the emitter voltage, keeping the current control switch 502 closed. The maximum duration of this operation may be limited by leakage currents; in general, selection of the components can be performed to ensure operation of the bootstrap circuit for at least as long as a phase of the output (approximately 5 to 30 milliseconds, or more or less, if desired). While the order of turn-on of the switches is not critical to the invention, it may be advantageous to provide the enable signals to the H-Bridge circuit elements before enabling the bootstrap circuit to allow a slower turn-on of the overall output, limiting "ground bounce" that can occur if a large voltage/current is driven to ground quickly; here, the combination of the intrinsic resistance in switch 502 and the size of resistor R1 534 and capacitor C1 532 provide a relatively slower turn-on than simply enabling the TRIAC 506 and/or SCR 512. To limit thermal effects, such turn on may preferably occur in a time frame of several microseconds, or more or less.

After the H-Bridge switches and switch 502 are enabled, current flows through the H-bridge high side switch 506 and patient load 510 and then exits through a low side switch 512 and reaches the parallel sense resistor 514 and shock switch 516. If the shock switch 516 is closed, the feedback line 518 remains at ground, and so the amplifier 520 does not close the pull down switch 540, and the current control switch 502 remains closed as the defibrillation shock is delivered. If the shock switch 516 is open, current passing through the patient load 510 is routed through the sense resistor 514, providing a voltage output to the amplifier 520 via line 518. If the feedback voltage from line 518 exceeds the voltage provided by the voltage divider 522/524, the amplifier 520 closes switch 540, reducing the gate voltage on current control switch 502 by draining capacitor 532 through resistors 534 and 538, until the amount of current flowing is reduced to a target constant current value. The circuit shown is simplified, and it will be understood by the skilled artisan that additional proportional/integral/differential control circuitry may be provide to stabilize the operation of the amplifier 520.

While a single voltage source is shown at 526, a plurality of sources may be used instead, or a variable source may be used. For example, the voltage provided to the amplifier in the feedback loop may be provided via a digital-to-analog convertor (DAC), allowing different current levels to be defined by digital control from a microcontroller for use in the constant current output mode.

FIGS. 9 and 10 are simplified diagrams that show additional control circuits for the current control switch. In FIG. 9, the circuit 600 includes a current control switch 602 coupling the HV capacitors 604 to the H-Bridge 606. An optoisolator 610 is used to deliver a voltage to the gate of the current control switch 602, while using a signal from the emitter side of the current control switch 602 to float appropriately above the system ground in order to continue controlling the switch 620. In this simplified circuit, it may be understood that a shock control signal can be provided from block 612 to the optoisolator 610, as well as a feedback signal 614, to provide control signals managing current flow to the appropriate output type. There are a wide variety of optoisolator types 610 which can be used in the circuit, each with different needs in terms of pulldown, pull-up, and grounding/isolation circuitry. The skilled artisan would readily be able to implement the added circuitry needed to provide further control. In some examples, the signal taken from the emitter side of the current control switch 602 may pass through one or more diode and/or capacitive devices (not shown).

FIG. 10 shows another example. Here a transformer 710 is used to provide DC isolation to a driver 716 that can receive inputs for shock control 712 and/or from feedback circuitry 714 placed on the low side of an H-bridge (as shown above in FIG. 8, for example). The transformer 710 may use a signal taken from the emitter side of the current control switch 702 to allow its isolated secondary side to float along with the gate of current control switch 702 relative to ground (as used here, secondary meaning the right side of the transformer as shown, rather than any labeled primary/secondary of the component 710). Rather than separate control signals each accessing the isolation component (the transformer 710), a driver 716 receives the separate control signals and provides one input to the primary side of the transformer.

Therapy decision making may include any of a variety of algorithms known in the art. In general, referring back to FIG. 1, the microcontroller 112 and associated memory and ASIC components may be adapted to receive electrical signals from the electrodes which are amplified and filtered to provide an input ECG signal. The input ECG signal can be compared to a time-varying threshold to detect heart beats, such as by detecting R-waves or QRS complexes in the cardiac signal. Such detections can be confirmed by analyzing for double detection and noise using known methods. The time elapsing between detected heart beats is recorded in order to calculate cardiac rate, which can be categorized suitable for a given system. For example, a pacemaker defibrillator may have a timeout period applied to detect long pauses between beats, indicating pacing should be delivered for bradycardia conditions. An adaptive pacemaker may use an input from, for example, a temperature sensor or motion detector, to adjust the timeout period to account for patient activity, allowing the paced heart rate to increase or decrease depending on patient activity. A defibrillator or tachyarrhythmia therapy system may also classify ventricular tachyarrhythmia (VT) and ventricular fibrillation (VF) rates, such as considering rates between 180 and 220 beats per minute (BPM) as VT, and rates above 220 BPM as VF (other rate threshold may be used, and the thresholds may be configurable by a physician or at a physician's request/order). VT rates may be used to trigger ATP, for systems that provide ATP and in which ATP is enabled. VF rates may trigger additional analysis for shock delivery, such as using an X/Y counter to determine how many beats (X) of a set of Y beats are deemed to indicate VF using, for example, shape analysis (morphology). Illustrative shape analysis techniques can include the use of correlation waveform analysis, in which a stored template of a "normal" beat electrical signature is compared to detected beats; low correlation may be deemed indicative of VF; detected beats may be compared one to another as well to differentiate VT from VF and/or to differentiate sinus tachycardia (resulting from exercise, for example) from VT and VF. Wavelet transformation analysis may also be used to analyze shape, as well as the width of beats. When VF is identified, preparations for defibrillation therapy can be commenced, including charging the capacitor stack to a defibrillation energy level (typically 30 Joules or more, and higher still if a subcutaneous-only system is used, where 60 Joules or more may be used).

In an example, a beat detection routine may be as described in U.S. Pat. No. 8,565,878, with cardiac signal analysis for overdetection performed as in U.S. Pat. No. 8,160,686. Arrhythmia discrimination may be performed using methods described in U.S. Pat. Nos. 6,754,528 and/or 7,330,757. With beats analyzed for arrhythmia, the overall rhythm may be assessed using methods as in US Patent Application Pub. No. 2006/01467503, and defibrillation therapy can be delivered when all requirements for defibrillation therapy have been met, meaning, for example and without limitation, that sufficient arrhythmic beats are detected in a persistent manner allowing positive confirmation of treatable arrhythmia. The disclosures of each of these patents and patent applications are incorporated herein by reference for at least the purposes identified for each. However, other methods may be used at each step, if desired, and the invention is not limited to use with these particular algorithms.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable defibrillator comprising a housing and operational circuitry therein, the operational circuitry comprising:
    at least one battery;
    at least one high power capacitor;
    a DC:DC conversion circuit configured to charge the at least one high power capacitor using current drawn from the at least one battery;
    an H-bridge output circuit comprising first and second high side legs and first and second low side legs, each leg comprising a switch, the first high side and first low side legs coupled together at a first output node, and the second high side and second low side legs coupled together at a second output node;
    a current monitoring subcircuit coupled to the first and second low side legs, the current monitoring subcircuit adapted to receive current through both of the first and second low side legs; and
    a current control subcircuit coupling the at least one high power capacitor to the first and second high side legs, the current control subcircuit configured to receive a feedback signal from the current monitoring subcircuit to control current through the H-bridge;
    wherein the current control subcircuit comprises a bootstrap circuit coupled to a first transistor that is configured to enable current flow to the H-bridge from the at least one high power capacitor.

2. The implantable defibrillator of claim 1 wherein the first transistor includes a gate, drain and source, the drain coupled to the high voltage power supply, the source coupled to the high side legs of the H-bridge; and the bootstrap circuit comprises:
    a first diode coupling the source of the first transistor to the gate of the first transistor;
    a capacitor coupled between the source of the first transistor and a second diode that in turn couples to a voltage source;
    a first resistor coupling a node between the second diode and the capacitor to the gate of the first transistor;
    a second transistor configured to receive a control signal related to a feedback signal captured by the current monitoring subcircuit; and
    a second resistor coupled via the second transistor to ground, the second resistor also coupled to the gate of the first transistor.

3. The implantable defibrillator of claim 1 wherein the bootstrap circuit comprises:
    a first transistor with a gate, drain and source, the drain coupled to the high voltage power supply, the source coupled to the high side legs of the H-bridge;
    a first diode coupling the source to the gate;
    a capacitor coupled between the source and a second diode that in turn couples to a voltage source;
    a first resistor coupling the node between the second diode and the capacitor to the gate;
    and a second transistor coupled to the gate of the first transistor, the second transistor configured to receive a control signal related to a feedback signal captured by the current monitoring subcircuit.

4. The implantable defibrillator of claim 1 wherein the current sensing circuit comprises a sense resistor coupled to the low side of the H-bridge to thereby create a voltage when current flows through the sense resistor, providing feedback to the current control circuit, further comprising a bypass path parallel to the sense resistor, the bypass path comprising one or more diodes allowing current to flow above a diode voltage, wherein the implantable defibrillator comprises a control module operable as follows:
    during defibrillation shock delivery, the feedback signal from the current sensing circuit is not used to control operation of the first transistor; and
    during pacing delivery, the feedback signal from the current sensing circuit is used to control operation of the first transistor.

5. The implantable defibrillator of claim 1 further comprising an enable switch, wherein the current control subcircuit comprises a first transistor for controlling current, wherein the enable switch couples the at least one high voltage capacitor to the first transistor, which in turn couples to the high side of the H-Bridge.

6. The implantable defibrillator of claim 1 further comprising an enable switch, wherein the current control subcircuit comprises a first transistor for controlling current, wherein the first transistor couples the at least one high voltage capacitor to the enable switch, which in turn couples to the high side of the H-Bridge.

7. An electronic circuit for providing an output in a medical device comprising:
    at least one high power capacitor;
    an H-bridge output circuit comprising first and second high side legs and first and second low side legs, each leg comprising a switch, the first high side and first low side legs coupled together at a first output node, and the second high side and second low side legs coupled together at a second output node;

a current monitoring subcircuit coupled to the first and second low side legs, the current monitoring subcircuit adapted to receive current through both of the first and second low side legs; and a current control subcircuit coupling the high power capacitor to the first and second high side legs, the current control subcircuit configured to receive a feedback signal from the current monitoring subcircuit to control current through the H-bridge;

wherein the current control subcircuit comprises a bootstrap circuit coupled to a first transistor that enables current flow to the H-bridge from the at least on high power capacitor.

8. The electronic circuit of claim 7 wherein the first transistor includes a gate, drain and source, the drain coupled to the high voltage power supply, the source coupled to the high side legs of the H-bridge; and the bootstrap circuit comprises:

a first diode coupling the source of the first transistor to the gate of the first transistor;

a capacitor coupled between the source of the first transistor and a second diode that in turn couples to a voltage source;

a first resistor coupling a node between the second diode and the capacitor to the gate of the first transistor;

a second transistor configured to receive a control signal related to a feedback signal captured by the current monitoring subcircuit; and a second resistor coupled via a second transistor to ground, the second resistor coupled to the gate of the first transistor.

9. The electronic circuit of claim 7 wherein the first transistor includes a gate, drain and source, the drain coupled to the high voltage power supply, the source coupled to the high side legs of the H-bridge; and the bootstrap circuit comprises:

a first diode coupling the source of the first transistor to the gate of the first transistor;

a capacitor coupled between the source of the first transistor and a second diode that in turn couples to a voltage source;

a first resistor coupling a node between the second diode and the capacitor to the gate of the first transistor; and a second transistor coupled to the gate of the first transistor, the second transistor configured to receive a control signal related to a feedback signal captured by the current monitoring subcircuit.

10. The electronic circuit of claim 7 wherein the current sensing circuit comprises a sense resistor coupled to the low side of the H-bridge to thereby create a voltage when current flows through the sense resistor, providing feedback to the current control circuit, further comprising a bypass path parallel to the sense resistor, the bypass path comprising one or more diodes allowing current to flow above a diode voltage, wherein the implantable defibrillator comprises a control module operable as follows:

during defibrillation shock delivery, the feedback signal from the current sensing circuit is not used to control operation of the first transistor; and during pacing delivery, the feedback signal from the current sensing circuit is used to control operation of the first transistor.

11. An electronic circuit for providing an output in a medical device comprising:

at least one high power capacitor;

an H-bridge output circuit comprising first and second high side legs and first and second low side legs, each leg comprising a switch, the first high side and first low side legs coupled together at a first output node, and the second high side and second low side legs coupled together at a second output node;

a current monitoring subcircuit coupled to the first and second low side legs, the current monitoring subcircuit adapted to receive current through both of the first and second low side legs; and a current control subcircuit coupling the high power capacitor to the first and second high side legs, the current control subcircuit configured to receive a feedback signal from the current monitoring subcircuit to control current through the H-bridge;

wherein the current control subcircuit comprises a high voltage isolation component having an input electrically coupled to the feedback signal from the current monitoring subcircuit, and an output floating relative to the input, wherein the output is delivered to a first transistor that controls current flow from the at least one high power capacitor to the H-bridge.

12. An electronic circuit for providing an output in a medical device comprising:

at least one high power capacitor;

an H-bridge output circuit comprising first and second high side legs and first and second low side legs, each leg comprising a switch, the first high side and first low side legs coupled together at a first output node, and the second high side and second low side legs coupled together at a second output node;

a current monitoring subcircuit coupled to the first and second low side legs, the current monitoring subcircuit adapted to receive current through both of the first and second low side legs;

a current control subcircuit coupling the high power capacitor to the first and second high side legs, the current control subcircuit configured to receive a feedback signal from the current monitoring subcircuit to control current through the H-bridge; and an enable switch, wherein the current control subcircuit comprises a first transistor for controlling current, wherein the enable switch couples the at least one high voltage capacitor to the first transistor, which in turn couples to the high side of the H-Bridge.

13. An electronic circuit for providing an output in a medical device comprising:

at least one high power capacitor;

an H-bridge output circuit comprising first and second high side legs and first and second low side legs, each leg comprising a switch, the first high side and first low side legs coupled together at a first output node, and the second high side and second low side legs coupled together at a second output node;

a current monitoring subcircuit coupled to the first and second low side legs, the current monitoring subcircuit adapted to receive current through both of the first and second low side legs;

a current control subcircuit coupling the high power capacitor to the first and second high side legs, the current control subcircuit configured to receive a feedback signal from the current monitoring subcircuit to control current through the H-bridge; and an enable switch, wherein the current control subcircuit comprises a first transistor for controlling current, wherein the first transistor couples the at least one high voltage capacitor to the enable switch, which in turn couples to the high side of the H-Bridge.

* * * * *